United States Patent
Mouret

Patent Number: 5,375,591
Date of Patent: Dec. 27, 1994

[54] INSTRUMENT FOR IMPLEMENTING MEDICAL OR SURGICAL OPERATIONS BY LAPAROSCOPY OR COELISCOOPY

[76] Inventor: Philippe Mouret, "Le Boujard", Sainte Euphemie, 01600 Trevoux, France

[21] Appl. No.: 923,979
[22] PCT Filed: Mar. 20, 1991
[86] PCT No.: PCT/FR91/00227
  § 371 Date: Sep. 17, 1992
  § 102(e) Date: Sep. 17, 1993
[87] PCT Pub. No.: WO91/14392
  PCT Pub. Date: Oct. 3, 1991

[30] Foreign Application Priority Data

Mar. 20, 1990 [FR] France .................. 90 03980

[51] Int. Cl.$^5$ ............................................. A61B 17/02
[52] U.S. Cl. ........................................ 128/20; 604/104; 606/191
[58] Field of Search ................. 128/20, 3, 17, 12; 606/190, 191, 198, 106; 604/104, 106–109

[56] References Cited

U.S. PATENT DOCUMENTS

| | | | |
|---|---|---|---|
| 1,798,124 | 3/1931 | Hunn | 128/20 |
| 2,221,138 | 5/1938 | Hendrickson | 606/191 |
| 3,099,544 | 7/1963 | Sheesley | 101/491 |
| 3,313,294 | 6/1964 | Uddenberg | 128/20 |
| 3,982,533 | 9/1976 | Wiest | 604/26 |
| 4,049,000 | 9/1977 | Williams | 128/20 X |
| 4,459,978 | 7/1984 | Kotsanis | 128/20 |
| 4,867,404 | 9/1989 | Harrington et al. | 128/20 X |
| 5,065,739 | 11/1991 | Forrest et al. | 128/20 |
| 5,183,033 | 2/1993 | Wilk | 128/20 |
| 5,289,817 | 3/1994 | Williams et al. | 128/20 |

FOREIGN PATENT DOCUMENTS

| | | |
|---|---|---|
| 2303512 | 10/1976 | France . |
| 2339936 | 8/1977 | France . |
| 661403 | 6/1938 | Germany . |

Primary Examiner—Richard J. Apley
Assistant Examiner—Donna Y. Maraglio
Attorney, Agent, or Firm—Herbert Dubno; Andrew Wilford

[57] ABSTRACT

An instrument for assisting surgical laparascopic or coelioscopic operations where the patient's anterior abdominal wall is formed with an aperture and is raised away from the patient's visceral organs comprises a wirelike body having a first part extending substantially in a plane and adapted to lie against the posterior face of the anterior abdominal wall, a second part extending transversely from the plane of the first part, having an outer end, and adapted to traverse the aperture in the abdominal wall, and a hook at the outer end of the second part adapted to be secured to a stationary support.

6 Claims, 2 Drawing Sheets

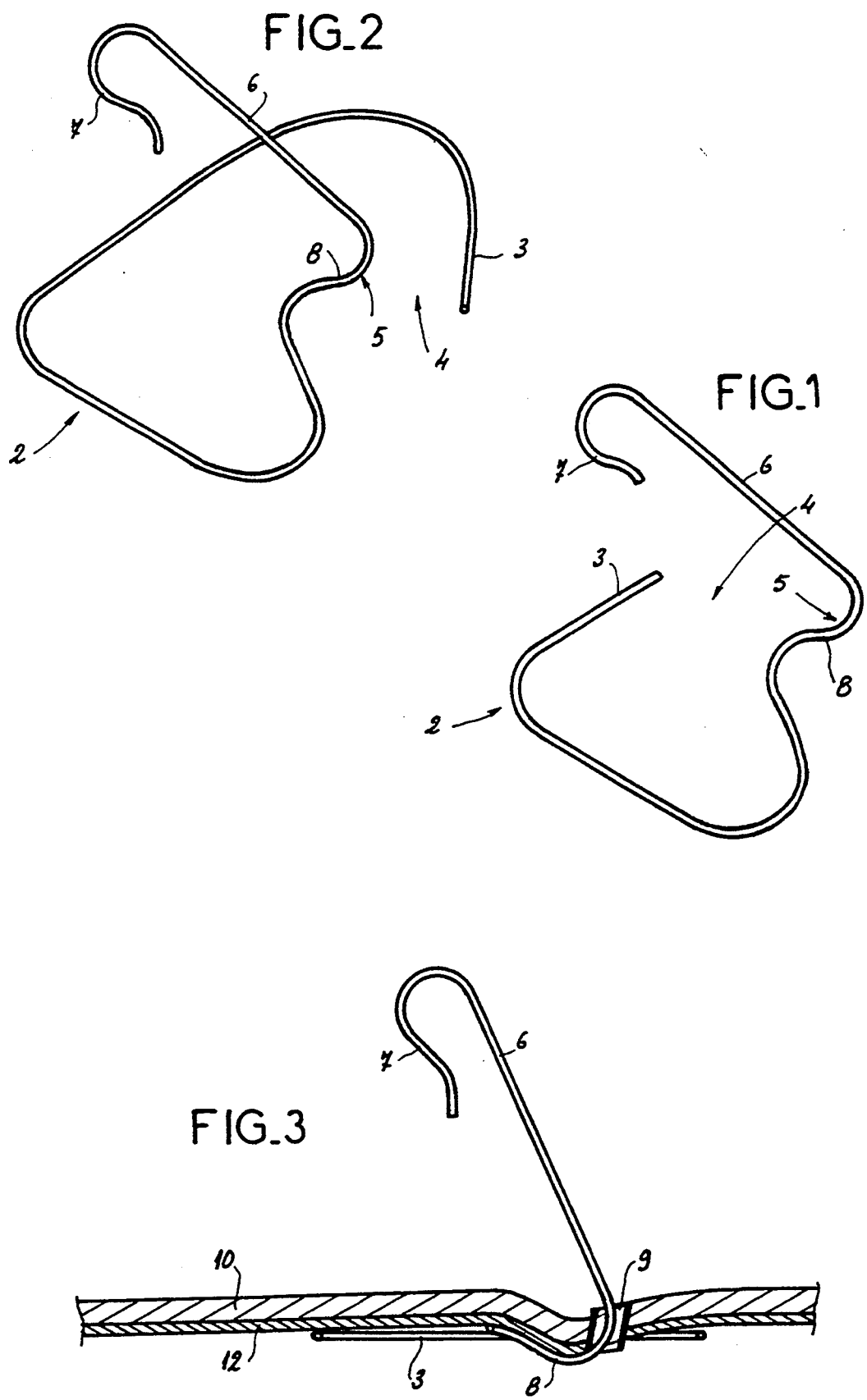

INSTRUMENT FOR IMPLEMENTING MEDICAL OR SURGICAL OPERATIONS BY LAPAROSCOPY OR COELISCOOPY

FIELD OF THE INVENTION

The subject of the present invention is an instrument for implementing medical or surgical operations by laparoscopy or coelioscopy.

BACKGROUND OF THE INVENTION

For the purpose of medical investigations, a coelioscopy technique is often employed, which consists in pressurising the volume delimited by the peritoneum, ensuring a raising of the abdominal wall, before introducing into the latter a trocar allowing passage of an optical device allowing visualisation of the state of the organs on which investigation is to be carried out.

It is also known to use this technique for carrying out surgical operations. In such a case it is suitable to make passages for several trocars of which some serve for visualising the organs on which the operation is to be carried out, and of which others serve for passage of the instruments.

The raising of the wall is currently obtained by a sufficient pressure difference between the peritoneal cavity and the outside. However this pressure difference cannot be increased without danger because of circulatory or ventilatory disturbances which this could cause.

Now, the plurality of the passageways causes gas leaks which are sufficiently large to prevent keeping a sufficient pressure inside the peritoneum. In fact, pneumoperitoneal insufflation apparatuses have a flow rate which is limited by construction, in particular for safety reasons. Furthermore, the increase of pressure inside the peritoneal cavity represents some danger during the course of a laparoscopy.

This constraint of relative airtightness requires that all the instruments used must be very specifically adapted so as to obtain as complete an airtightness as possible in the crossing of the wall. This extremely rigorous technical constraint is a very restricting factor in the design and production of coelioscopic surgical instruments.

Moreover, the appearance of operating techniques comprising the ablation of tissue volume or of larger organs requires the creation of extraction orifices of greater size than those normally used in conventional laparoscopy. These extraction orifices generate considerable leaks from the pneumoperitoneum which cause collapse of the wall, which is manifested by an complete disappearance of the operating volume as well as the zone of visibility for the practitioner.

OBJECTS OF THE INVENTION

The present invention aims to alleviate these problems by providing an instrument allowing the raising of the wall of the peritoneum to be held mechanically.

For this purpose, the instrument to which it relates is made from a filiform material and comprises a first part intended to be positioned against the deep surface of the anterior abdominal wall, and a second part which, crossing the abdominal wall, is terminated by a fastening device.

According to a first embodiment, this instrument is made from a fillform material and comprises a first part generally in the shape of an open ring intended to be positioned against the deep surface of the anterior abdominal wall, and a suspension element crossing the abdominal wall and terminated by a fastening device.

In practice, the peritoneal cavity is pressurised and equipped with a flexible trocar which crosses the abdominal wall. By means of this flexible trocar the ring-shaped; part of the instrument is introduced, from the open free end of this part, until that ring-shaped part is positioned against the deep surface of the anterior abdominal wall. The suspension element which terminates in a fastening device, for example in the shape of a hook, is then solidly attached to a support such as a bracket attached to the operating table. It is thus possible to hold the abdominal wall mechanically, so that one no longer depends exclusively on the insufflation of gas inside the peritoneal cavity.

In order to facilitate ring-shaped introduction through the abdominal wall, this ring-shaped part is disposed in a slightly twisted plane, the end zone of the branch forming the open part of the ring being inclined with respect to the plane of the latter, on the side opposite the suspension element.

The shape of the ring is not necessarily circular but adapted to the type of suspension which is to be carried out, it being necessary for the width of the opening of the ring to be sufficient to allow crossing of the wall without traumatizing the tissue.

According to another characteristic of the invention, the instrument is made from an elastically deformable material. This may consist of stainless steel or a synthetic material. The essential requirement is that the instrument be made from a material which is sufficiently rigid to fulfil its function, that is to say to support a traction which keeps the degree of parietal raising desired whilst being sufficiently elastic and deformable to facilitate the operations of introduction into the cavity and to avoid traumatisation of the tissue.

According to one embodiment, the instrument is made from a tubular element capable of being connected to a source for supplying the peritoneal cavity with gas. The instrument then performs a double function, on the one hand of mechanical holding of the abdominal wall, and on the other hand of a pipe for conveying gas maintaining an overpressure in this cavity, in order to avoid entry of air.

According to another characteristic of the invention, the suspension element makes an acute angle with the plane of the ring. This angle allows the ring-shaped part to be disposed at an angle with respect to the wall, in order to give maximum field of view along the axis of sight of the coelioscope.

According to another characteristic of the invention, the ring-shaped part situated substantially in a plane is connected to the suspension element by a curvilinear segment, extending beyond the plane of the ring on the side opposite that which the suspension element extends beyond. This curvilinear segment forms a hollow part in which a part of the abdominal wall engages, allowing stabilisation of the instrument when the latter is in traction, and avoiding any risk of sliding. It should be noted in general that all the curves of the instrument must be of a sufficient radius in order to avoid straining the tissue during the introduction operations.

According to another characteristic, the suspension element is fitted with a handle or the like allowing easy manipulation of the instrument during the phase of introducing the ring into the peritoneal cavity.

According to one possibility, the instrument is made in two parts joined together but separable at the level of the suspension element. This characteristic makes the instrument dismantleable, which is advantageous in order to carry out the operations of cleaning and also of sterilisation.

According to another embodiment, this instrument comprises a straight tubular branch which, intended to cross the abdominal wall, is extended at one of its ends by a branch making an angle with it, and intended to bear against the deep surface of the abdominal wall and at its other end by a suspension terminated by a fastening device, the tubular branch serving for housing and guiding in rotation a shaft of which one end is equipped with at least one branch which can be moved during the pivoting of the shaft between a position in which it is in contact with the branch and a position in which it makes an angle with the latter, and of which the other end is equipped with an operating lever extending beyond the tubular branch.

BRIEF DESCRIPTION OF THE DRAWING

In any case, the invention will be better understood with the help of the description with reference to the attached diagrammatic drawings which represent by way of non-limiting examples three embodiments of this instrument:

FIG. 1 is a perspective view of a first instrument;

FIG. 2 is a perspective view of a second instrument;

FIG. 3 is a view of the instrument in FIG. 2 in the position of use; and

SPECIFIC DESCRIPTION

Figure 4:
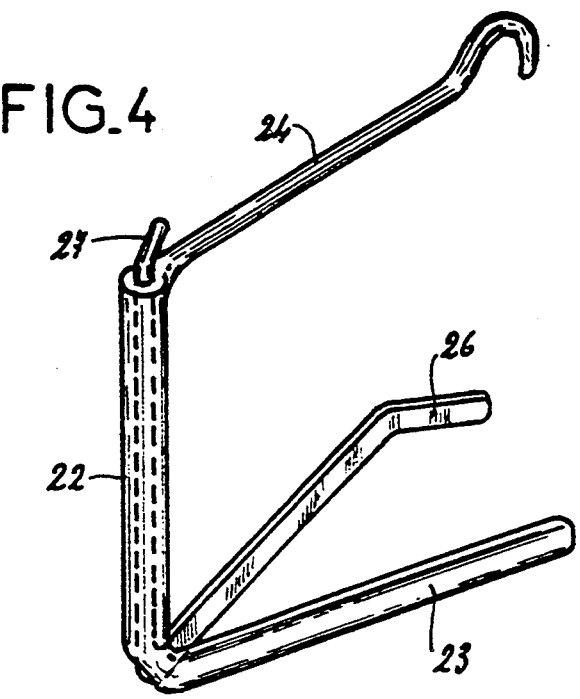
FIGS. 4 and 5 are two perspective views of another instrument in two positions.

The instrument represented in FIG. 1 comprises a part 2 in the shape of an open ring, situated substantially in a plane, of which the free end is part of a branch 3 which is slightly inclined with respect to the plane of the ring. The free end delimits with the other end of the ring an opening 4 of which the width is at least the thickness of the abdominal wall. The other end of the ring, designated by the reference 5, is equipped with an extension constituted by a suspension element 6 of which the free end terminates in a hook 7 intended for example to be fixed to a bracket or another support solidly attached to the operating table. The part of the ring situated in a plane is connected to the suspension element by a curvilinear segment 8 which projects with respect to the plane of the ring, on the side opposite the suspension element 6.

In practice, the instrument is engaged by its branch 3 inside a flexible trocar 9 in the peritoneal cavity, a movement being made in order for the whole of the ring to bear against the anterior surface of the abdominal wall 10, as shown in FIG. 3. During this operation, the peritoneal cavity, of which the peritoneum 12 is represented in the drawing, is inflated to raise the wall 10 and peritoneum 12. Then the hook 7 is engaged over a bracket to hold the wall 10 and peritoneum 12 up and the pressurization can be stopped, leaving the wall 10 and peritoneum 12 elevated.

It is apparent by comparing FIGS. 1 and 2, in which the same elements are designated by the same references, that the ring 2 may have two different shapes. It is also important to note that the suspension element 6 forms an acute angle with the plane of the open ring 2, so that the elevation of the wall can be greater in the zone in which the coelioscope is oriented. Finally, as is clearly apparent in FIG. 3, the abdominal wall presses on the bottom of the curvilinear segment 8, which avoids any risk of sliding of the instrument against this wall during the operation.

Figure 5:
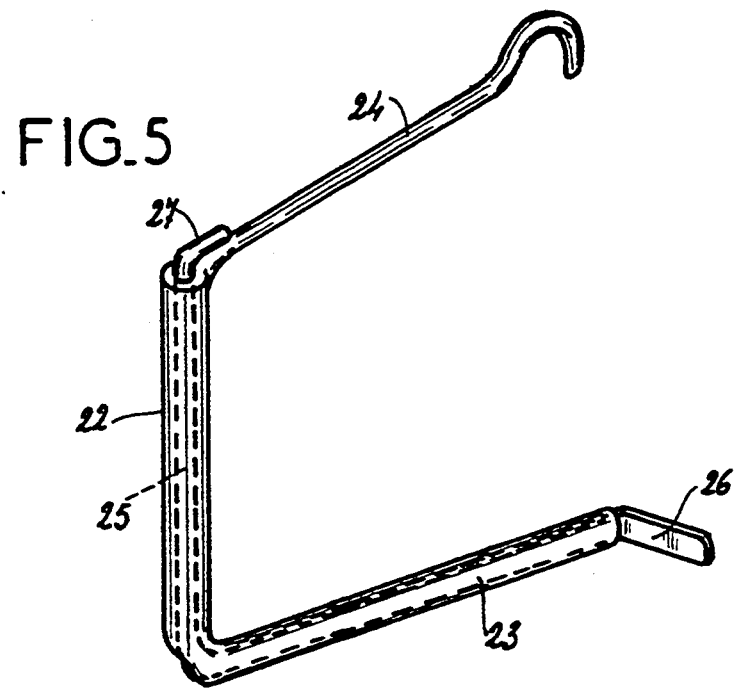

FIGS. 4 and 5 represent another embodiment of this instrument. The latter comprises a straight tubular branch 22 which, intended to cross the abdominal wall, is extended at one of its ends by a branch 23 making an acute angle with it, intended to bear against the deep surface of the abdominal wall. At its other end, the branch 22 is equipped with a suspension arm 24 terminated by a fastening device.

The tubular branch 22 serves for housing and guiding in rotation a shaft 25 of which one end is equipped with a branch 26 disposed at the level of the branch 23, and of which the other end is equipped with an operating lever 27 extending beyond the tubular branch 22.

The branch 26, by actuating the lever 27, can thus be pivoted between a position, represented in FIG. 5, in which it is contiguous with the branch 23, in order to carry out the crossing of the abdominal wall, and a position, represented in FIG. 4, in which makes an angle with the branch 23, corresponding to the position for supporting the abdominal wall.

It would be possible in a variant to envisage more than two branches for the support of the abdominal wall.

In the embodiments of FIGS. 1-3 the instrument is constituted by a solid wire and made in a single piece, for example made from stainless steel. However this instrument may be equipped with a handle at the region of the hook 7 to facilitate handling of the instrument and the handle can be tubular so gas can be passed through it to the peritoneal cavity, or can also be made in several dismantleable parts in order to facilitate its storage and sterilisation.

As is apparent from the above, the invention brings a great improvement to the existing technique of raising the abdominal wall by providing an instrument ensuring mechanical support of the abdominal wall. This avoids the need for keeping a gaseous pressure inside the peritoneal cavity for a long period of time, which can be difficult to maintain in the case of leakage, and which can cause the patient circulatory and ventilatory disruption.

As is obvious, the invention is not limited to the embodiments of this instrument which are only described above by way of examples, it encompasses, on the contrary, all variants thereof.

I claim:

1. A surgical instrument for assisting laparascopic or coelioscopic operations where the patient's anterior abdominal wall is provided with an aperture and is raised away from the patient's visceral organs, the instrument comprising:

a first wire-body part extending substantially in a plane and adapted to lie against the posterior face of the anterior abdominal wall of the patient, a second wire-body part extending transversely from the plane of the first part, having an outer-end, and adapted to traverse the aperture in the abdominal wall, and a suspension hook at the outer end of the second part adapted to be secured to a stationary support so as to raise the abdominal wall away from the internal organs of the patient.

2. The instrument defined in claim 1 wherein the first part is formed as an open ring.

3. The instrument defined in claim 2 wherein the ring has an end portion attached to the second part and inclined away from the second part and from the plane of the first part.

4. The instrument defined in claim 1 wherein the first and second parts are elastically deformable.

5. The instrument defined in claim 2 wherein the second part extends at an acute angle to the plane of the ring.

6. The instrument defined in claim 2 wherein the ring has a curved end portion attached to the second part and open toward the plane and toward the second part.

* * * * *